US005163451A

United States Patent [19]

Grellas

[11] Patent Number: 5,163,451

[45] Date of Patent: Nov. 17, 1992

[54] REHABILITATION PATIENT POSITIONING METHOD

[75] Inventor: Demosthenes Grellas, Los Gatos, Calif.

[73] Assignee: Sutter Corporation, San Diego, Calif.

[21] Appl. No.: 826,305

[22] Filed: Jan. 24, 1992

Related U.S. Application Data

[60] Division of Ser. No. 776,974, Oct. 15, 1991, and a continuation-in-part of Ser. No. 630,068, Dec. 19, 1990, abandoned.

[51] Int. Cl.[5] ........................ A61B 19/00; A61H 1/02

[52] U.S. Cl. .................................. 128/898; 128/25 R

[58] Field of Search ..................... 128/25 R, 25 B, 26, 128/898; 297/188, 217, 170-172, 423

[56] References Cited

U.S. PATENT DOCUMENTS

| | | | |
|---|---|---|---|
| 2,620,863 | 12/1952 | Cooper | 297/188 |
| 3,601,443 | 8/1971 | Jones | 297/188 |
| 3,712,669 | 1/1973 | Cates | 297/188 |
| 3,832,001 | 8/1974 | Robinson | 297/188 |
| 3,991,749 | 11/1976 | Zent | 128/26 X |
| 4,222,376 | 9/1980 | Praprotnik | 128/25 R |
| 4,285,515 | 8/1981 | Gezari . | |
| 4,372,551 | 2/1983 | Yurdin . | |
| 4,577,623 | 3/1986 | Pecheux | 128/25 R |
| 4,645,167 | 2/1987 | Hardwick | 297/188 X |
| 4,671,257 | 6/1987 | Kaiser et al. | 128/25 R |
| 4,767,159 | 8/1988 | Opsuik | 297/423 |
| 4,767,160 | 8/1988 | Mengshoel et al. | 297/172 X |
| 4,773,398 | 9/1988 | Tatom | 128/25 R |
| 4,776,583 | 10/1988 | Jennings . | |
| 4,779,922 | 10/1988 | Cooper | 297/188 |
| 4,798,411 | 1/1989 | Lin | 297/170 |
| 4,802,462 | 2/1989 | Reiss et al. | 128/25 R |
| 4,854,301 | 8/1989 | Nakajima | 297/188 X |
| 4,915,450 | 4/1990 | Cooper | 297/423 |
| 4,981,131 | 1/1991 | Hazard | 128/38 |

FOREIGN PATENT DOCUMENTS

| | | | |
|---|---|---|---|
| 0251643 | 1/1988 | European Pat. Off. | 297/217 |
| 729928 | 8/1932 | France | 297/188 |
| 2010667 | 7/1979 | United Kingdom | 297/188 |

*Primary Examiner*—Vincent Millin
*Assistant Examiner*—Linda C. M. Dvorak
*Attorney, Agent, or Firm*—Jacques M. Dulin; Thomas C. Feix

[57] ABSTRACT

Patient support and positioning system for continuous passive motion (CPM) machines comprising a fully adjustable chair to which is attached a horizontal telescoping arm having a coupling member for fastening the vertical stand of a CPM machine thereto. The chair has full adjustment in all axes; rotation around a vertical center axis; vertical height adjustment; fully adjustable seat back, both fore-and-aft and vertically for proper lumbar support; and tilt of the seat. The telescoping arm is lockably adjustable in length to provide proper center-to-center distance between the center post of the chair and the CPM machine support. The arm further includes a downward vertical step member at its outboard CPM machine connecting end to permit proper vertical alignment of the CPM machine for users having a short torso. The arm also provides a support for a CPM power supply/control unit, and has means for securing the power cord out of the way off the floor. The invention permits support of the patient with a full range of adjustment so that the patient can have proper positioning for selected exercise of the selected extremity in flexion/extension, forward flexion/extension internal/external rotation, supination/pronation and the like.

13 Claims, 3 Drawing Sheets

REHABILITATION PATIENT POSITIONING METHOD

CROSS REFERENCE TO RELATED APPLICATIONS

This is a continuation-in-part of my earlier application Ser. No. 630,068 filed Dec. 19, 1990, now abandoned, for Rehabilitation Patient Positioning Device, the benefit of the filing date of which is claimed under 35 U.S.C. 120. This application is a divisional application of Ser. No. 07/776,974, allowed.

FIELD

This invention relates generally to rehabilitation devices, and more specifically to specialized patient support and positioning assemblies for use in association with continuous passive motion machines that provide motor-assisted motion to injured extremities, for example the arm, shoulder and wrist in order to exercise the extremities to build muscle strength and tissue.

BACKGROUND

Many injuries to joints result in long term disuse in order for the joint structures to heal. A result of this is that there is joint stiffness and possible muscular atrophy which must be restored for the patient to reacquire extremity usage. For example, considering rotator cuff injuries of baseball or football players or elderly patients with various bone fractures or arthritis, these type of patients need to have power-assisted exercise of the joints and associated musculature in order to rebuild the muscles for functional use.

A number of machines currently exist to provide for the appropriate joint exercise For example, Pechuex U.S. Pat. No. 4,577,623 illustrates a continuous passive motion (hereinafter "CPM") device for upper extremities which exercises the shoulder and arm. This machine provides for forward flexion/extension, abduction/adduction with or without external/internal rotation of the shoulder by means of various motor-driven levers, pulley and cable systems.

The Pecheux machine is currently commercially available as the kinetic brand shoulder CPM machine made by COGEMO S.A. of Tournes, France, and distributed by Richards Medical Company of Memphis, Tenn. The machine is mounted on a vertical shaft fastened to a four-legged horizontal base having castors. Two of the legs are short and extend outboard of the machine, and the two other legs are substantially longer in order to extend underneath a chair provided by a patient. The long pair of legs also prevents the device from tipping over, it being necessary to spread the weight since the CPM unit has several active arms and other elements which are cantilevered out from the center line of the vertical support post. Accordingly, the entire unit needs to be counter-balanced by the long legs. COGEMO also offers, through Richards Medical Company, an elbow CPM for passive flexion/extension of the elbow without associated pronation/supination of the wrist.

These CPM devices are current state of the art for both passive and active resistive therapy for a variety of surgical and chronic etiologies. But they pose problems in proper utilization for specific therapy requirements, because proper patient positioning with respect to the machine is important, if not critical. In many instances, the patient uses this machine by him/herself at home after limited instruction. The chair is usually provided by the patient Because both the height, size and nature of the chair used by the patient and the size and mobility of the patient ranges widely, patient positioning problems become significant. Further, after the physical therapist leaves the patient, the patient may shift the chair with respect to the machine, and what becomes prescribed passive abduction/adduction of the shoulder with or without associated external/internal rotation could drift into an external or internal rotation motion that is not prescribed. Further, the patient may move too far away from the machine, thus encouraging spinal curvature and discomfort. Usually the chair does not have appropriate lumbar support, thus aggravating an independent or associated spinal condition during rehabilitation.

In addition, because of the length and spread of the base leg assembly of the CPM unit, and the leg height off the floor, the unit can not accept many kinds of chairs, or the position of the patient with respect to the chair is constrained and awkward. That is, the patient must sit on the chair in an unnatural position because the chair will not fit properly with respect to the machine. This leads to improper or incomplete exercise, or leads to early fatigue of the patient. Further, the patient becomes discouraged from use of the rehabilitation unit, and rehabilitation is delayed or becomes counter-productive. These are just a few of the problems which arise because of the construction of the current state of the art CPM machines.

Accordingly, there is a need in the art for an accurate positioning system which properly positions the patient in the correct posture and the correct distance from the machine, yet which is adjustable along all axes to provide for a full range of active and passive resistive therapy for a wide variety of surgical, chronic and age-related etiologies, yet is both totally adaptable to specific therapy requirements and allows for progressive changes in therapy, and which once positioned by the rehabilitation specialist is not subject to inadvertent patient change leading to improper positioning and use.

THE INVENTION

Objects

It is among the objects of this invention to provide an improved patient positioning system for use in association with CPM machines for active and passive rehabilitative exercise of patient extremities.

It is another object of this invention to provide a special stand and chair system which can accept, in the proper relative position, a CPM machine thereby affording a complete range of positioning of the patient along all axes with respect to the machine for a wide variety of surgical and chronic etiologies, and which is both fully adaptable to specific therapy requirements and allows for progressive changes in therapy, without the patient inadvertently interfering with the setting once properly positioned by the therapist.

It is another object of this invention to provide a rehabilitation device having a patient positioning chair with lumbar support, lockable swivel rotation, tilt and height adjustment capability, which includes a special arm for proper support in the appropriate orientation of a CPM unit as well as the associated electronics.

Still further and other objects will be evident from the specification, drawings and claims.

DRAWINGS

The invention is illustrated in the accompanying drawings in which.

SUMMARY

Figure 1:
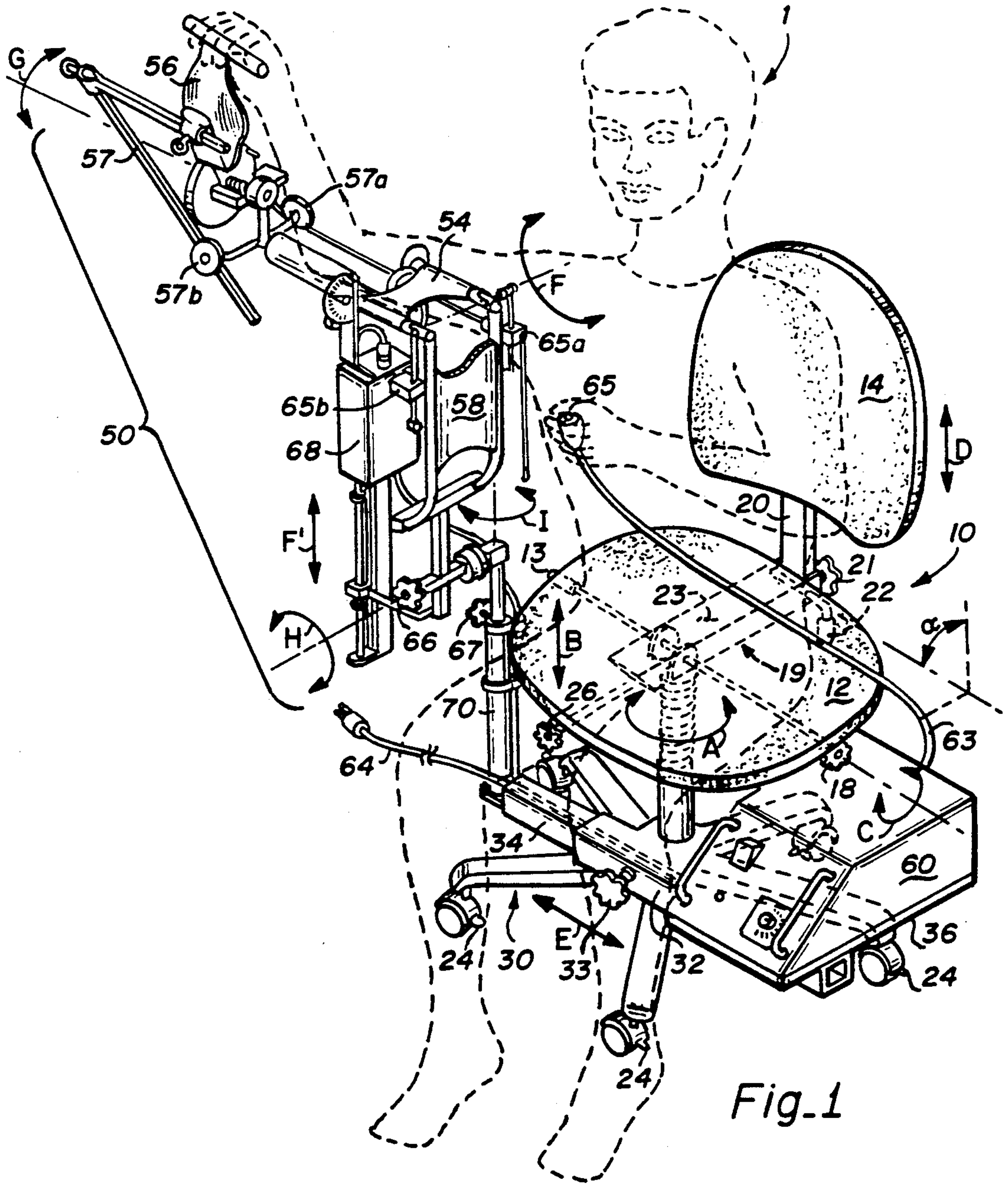
FIG. 1 is an isometric view of the patient positioning device of this invention showing its relation to an upper extremity CPM machine and showing a patient (in phantom) positioned thereon.

The invention comprises a patient support and positioning assembly for use in connection with continuous passive motion (CPM) machines, which assembly permits precise positioning of the patient in multiple axes with respect to a CPM machine for rehabilitation of one or more extremities of a patient.

The patient positioning system of this invention comprises three basic parts: A chair assembly; a telescoping arm assembly; and a CPM machine received in and supported by the arm assembly. The chair and arm assembly cooperatingly properly position the patient with respect to the CPM unit to provide a full range of rehabilitative motion for an extremity. The exemplary disclosure here is that of an upper extremity CPM machine, and more particularly with respect to either a shoulder or arm machine, but it should be understood that any CPM unit including those for lower extremities may be employed.

The chair is constructed to provide rotation of the seat in a generally horizontal plane around a vertical central axis, with the angle of rotation optionally and preferably adjustably lockable in a fixed angular relation to the CPM unit after appropriate patient positioning. The chair seat is also vertically adjustable for height, and may be lockable at any particular height level. Preferably a conventional gas-lift air support column is employed which permits ease of use by simple lever action release of the gas valve. In addition, the chair includes a fully adjustable lumbar back support. The seat of the chair optionally is adapted to tilt around a horizontal axis. The chair central column is joined to a star-type or spider-type multi-arm castor-bearing base. The castors optionally and preferably are of the lockable type.

The arm is a telescoping type arm, preferably hollow to permit the threading therethrough and retaining of electrical wiring for the power and control unit of the CPM. The arm is generally disposed horizontally, and is preferably secured to the chair by a U clamp assembly at the juncture of the vertical chair column and the base. The arm is generally tangent to the chair center column, and may lie either in front or in back of it, although any orientation with respect to the chair seat is possible in view of the fact that chair seat and base are rotatable 360° with respect to each other.

The opposed outboard ends of the telescoping arm unit serve different purposes. One outboard end carries a fitting to receive the lower end of the CPM unit, and maintain the adjustable main support of the CPM unit in a true vertical position. In the preferred best mode, the CPM unit fitting is dropped vertically a few inches relative to the telescoping arm unit by the addition of a downwardly stepped extension member to permit shorter people, (i.e., people having shorter torsos) easier access to the CPM machine so that an uncomfortable exercise position does not occur (i.e. where the elbow is exercised at a position where it is pointed upward). The height adjustment of the CPM machine may then be fine tuned by activating the gas lift cylinder knob associated with the support arm of the CPM machine.

The opposite outboard end preferably contains a plate or other means for holding the power supply and other associated operative controls, such as rate of lift, for the CPM unit. This permits the control box of the CPM unit to be tucked under the chair out of the way. The power cord from an electrical outlet is fed directly to the CPM power/control box which contains a transformer to convert the 110 or 220 voltage to 24 volts to power the low voltage motor that causes the elevation and/or rotation of the various actuators of the CPM unit. The 24 volt power supply cord from the transformer control box to the motors on the CPM unit can be led through a hole in the telescoping arm adjacent the control box support plate, and thence out the outboard end of the arm having the fitting for supporting the center column of the CPM unit. Optionally, one or more clips can secure the 24 volt power cord to the side of the CPM support shaft.

In the preferred best mode, a sheath is provided to enclose and protect the power cords to the motor and a pair of velcro straps, each being fixed to the telescoping arm unit, are then tightened to secure the loose power cords to the side surface of the arm unit.

The telescoping lateral arm has a locking knob that locks the extension portion of the telescoping assembly in position once the center-to-center distance between the center post of the chair and the support post of the CPM unit is selected. This distance can be infinitely varied, and the angular relationship between a vertical plane passing through both shoulder joints of the patient and the brachial cradle of the CPM can be also infinitely adjusted by the rotation of the chair seat. The chair seat can then be locked into the appropriate position. If desired, the unique distance and angle for each particular patient can be expressed in polar coordinates. The chair back can then be adjusted to assure the proper posture of the patient. For a knee and/or leg CPM machine, the chair seat can be tilted back if required. Thus, full positioning adjustment in all axes is possible for the patient employing the positioning system of this invention with respect to a wide variety of CPM machines.

DETAILED DESCRIPTION OF THE INVENTION

The following detailed description illustrates the invention by way of example, not by way of limitation of the principles of the invention. This description will clearly enable one skilled in the art to make and use the invention, and describes several embodiments, adaptations, variations, alternatives and uses of the invention, including what I presently believe is the best mode of carrying out the invention.

Figure 2:
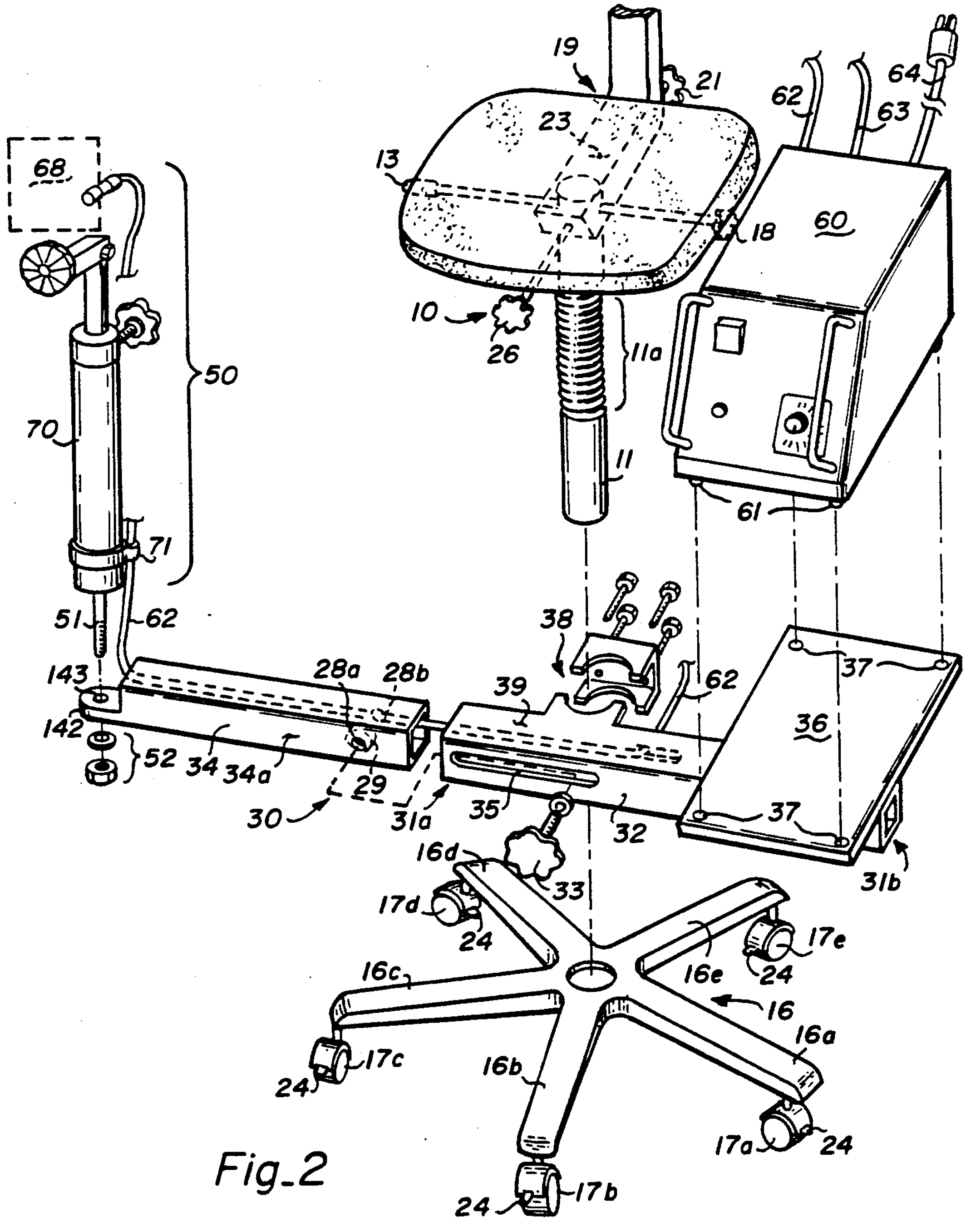
FIG. 2 is an exploded perspective of the positioning device of this invention.

A rehabilitation patient positioning device constructed in accordance with a preferred embodiment of the present invention is shown in FIGS. 1 and 2 and generally designated by reference numeral 1.

The rehabilitation patient positioning device 1 generally comprises a multi-positional chair assembly 10 and an arm assembly 30 associated with the center post 11 of the chair assembly 10. A commercially available CPM machine 50 is positioned relative to and spaced from the chair assembly 10 by the arm assembly 30. The description of the above 3 major assemblies will first be discussed individually.

CHAIR ASSEMBLY

The chair assembly 10, being substantially similar to a conventional secretarial-type chair, further comprises a seat 12, a back rest 14, the aforementioned center post 11 and a five-legged, star-pattern base support 16. Each leg **16*a*–16*e* of the base support 16 has provided thereon a caster member 17*a*–17*e* to permit easy transferability and of the rehab patient positioning device 1** to any desired situs.

The chair assembly 10 is permitted to swivel 360° about the axis of center post 11 as indicated by arrow A. Height adjustment of the chair assembly is accomplished by operator actuation of gas lift lever 13 which raises or lowers the seat 12 which extends or shortens an adjustable portion **11*a* of center post 11**. This height adjust movement is indicated by arrow B.

The swivel movement of the center post 11 may be locked in any selected position by actuation of a swivel lock knob 26. The chair assembly also includes a multi-adjustable tilt knob 18 which upon actuation will tilt the chair assembly 10 back to a desired tilt position in the direction as shown by reference to arrow C.

A support assembly 19, including horizontal member 23 and vertical upright 20, connects the backrest 14 to the seat 12. The back rest 14 is contoured to provide lumbar support for a user's back and may be angularly positioned with respect to the seat 12 over an angular range of about 85° to about 120° by actuation of an adjusting lever 22 provided on the support assembly 19. This range of angular adjustment is best seen by reference to angle $\alpha$ in FIG. 1. The height of back rest 14 with respect to seat 12 is also vertically adjustable by user actuation of knob 21 on vertical upright 20. This vertical adjustment is shown by reference to arrow D.

ARM ASSEMBLY

As is best seen in FIG. 2, the arm assembly 30 comprises a box-channel sleeve member 32 having a hollow rod or tube 34 adapted to be in telescoping engagement with a first end **31*a* and a control unit supporting platform 36 associated with a second end 31*b* of the sleeve 32**.

The sleeve member 32 includes a bracket assembly 38 disposed medial of the telescoping end of sleeve 32 and integrally attached thereto and which is adapted to clamp onto a lower portion of the center post 11 so that the bracket assembly 38 is bottom supported by the five-legged base support 16. The platform 36 is dimensioned to provide a base support for a control unit 60 associated with a commercially available CPM machine 50 and includes four corner disposed bore holes 37 that are adapted to receivingly engage and snugly retain four rubber feet supports 61 associated with the underside of control unit 60.

It is understood that the arm assembly 30 may be attached to the chair assembly 10 in various other ways including but not limited to forming the arm assembly 30 integrally with the base support 16.

It is important to note that the platform 36 when supporting control unit 60 has a combined weight which serves to counter balance the CPM machine 50 when supported on the outboard end of rod 34 and thus stabilizes the overall assembly.

As is best seen in FIG. 1, the arm assembly 30 is laterally adjustable in the direction as shown by the arrow E by actuation of knob 33. In the alternate embodiment of FIGS. 1 and 2 as well as the preferred embodiment of FIG. 5, the range of the telescoping extension of rod 34 with respect to sleeve 32 is provided by slot 35 in a forward vertical side wall of sleeve 32. In the FIG. 1 and 2 embodiment, rod 34 is provided with a threaded hole **28*a* on a first forward facing vertical surface 34*a* and an axially aligned and slightly larger diameter unthreaded hole 28*b* on its other vertical surface. Both holes of rod 34 are adapted to receive a threaded screw portion of knob 33. In the preferred embodiment of FIG. 5, a lock nut 29 (see FIG. 2) is spot welded to the inside surface of vertical wall 34*a* in alignment with threaded hole 28*a*. Knob 33 is provided with a shorter threaded shaft to permit a sufficiently rigid engagement between sleeve 32 and rod 34 when knob 33 is inserted within threaded hole 28*a*** and tightened down by a clockwise rotation.

In use, rod 34 is inserted, within sleeve 32 so that a portion of slot 35 is aligned with threaded hole **28*a*. Then the threaded portion of knob 33 is directed through both slot 35 and threaded hole 28*a* until the threaded end of knob 33 passes through hole 28*b* and abuts the inner surface of vertical side wall 39 of sleeve 32. A lateral adjustment of the arm assembly 30 is made by loosening knob 33 and extending or retracting rod 34 with respect to sleeve 32 until a desired lateral extension of the arm assembly 30 is achieved after which knob 33 is then retightened to make rigid the arm assembly 30**.

A tongue 142 is attached to the outboard or free end of rod or tube 34 and has a bore hole 143 adapted to receive a threaded end 51 associated with the lower shaft 70 of a CPM machine 50. A washer and nut assembly 52 secures the threaded end 51 to the tongue 142.

The sleeve 32 is also provided with a hole 40 along its rearward vertical face 39 to permit internal routing of certain electrical cords which are connected to the back of control unit 60. For example, the patch cord 62, which connects the control unit 60 to the electrical motor 68 of the CPM machine, is internally routed through the arm assembly 30 by first entering the sleeve assembly at hole 40 and then exiting the rod assembly at the outboard or free end of rod 34 where it is then vertically routed along the side wall of shaft 70 and secured thereto by one or more clamps 71 before it is terminally connected to the electric motor 68. Similarly, the electrical outlet cord/plug 64 may be internally routed through the arm assembly 30 so that it exits the free end of the hollow rod assembly where it then can be plugged into any convenient located electrical outlet (see FIG. 1).

A hand control unit 65 for the CPM machine 50 is connected to the control unit 60 by an umbilical 63 and is permitted to dangle freely so that it may be used in a number of positions by the user's free hand. It should be noted, however, that the umbilical 63 may also be internally routed through the arm assembly 30 in a manner similar to patch cord 62 (and optionally outlet cord 64) and secured to shaft 70 by one or more clamps 71 so that a sufficient length of the umbilical 63 remains for the convenient use of the user's free hand. Internal routing through the arm assembly 30 of all cables in this manner provides a clean look to the rehab patient positioning device 1 of the present invention as well as eliminating any trip hazard that may result from loose or tangled electrical cords. It should also be noted that a sufficient amount of cord slack should be maintained within the hollow interior of the arm assembly to permit the rod 34 to be telescopingly extended without binding or stretching of the internally routed cords.

Figure 3:
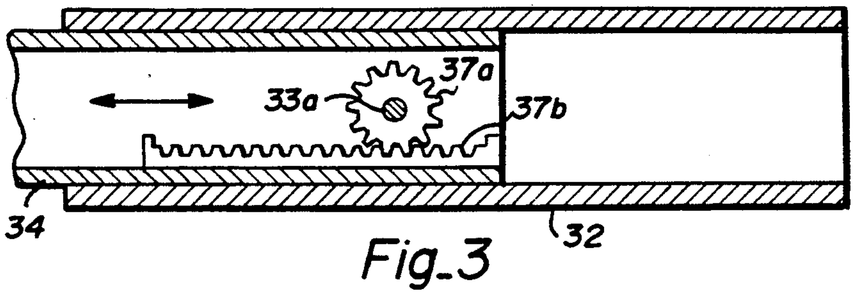
FIG. 3 is a vertical, partial section view showing a rack and pinion advancement/retraction mechanism for the telescoping tube of the arm assembly.

As shown in FIG. 3, in an alternate embodiment of the telescoping arm assembly, the tube 34 is horizontally adjustable by a rack and pinion assembly. The locking knob 33 is journaled in a hole rather than a slot 35 and shaft 33*a* is shortened and carries a pinion gear 37*a* which engages a toothed rack 37*b* in the bottom of the tube 34.

Figure 4:
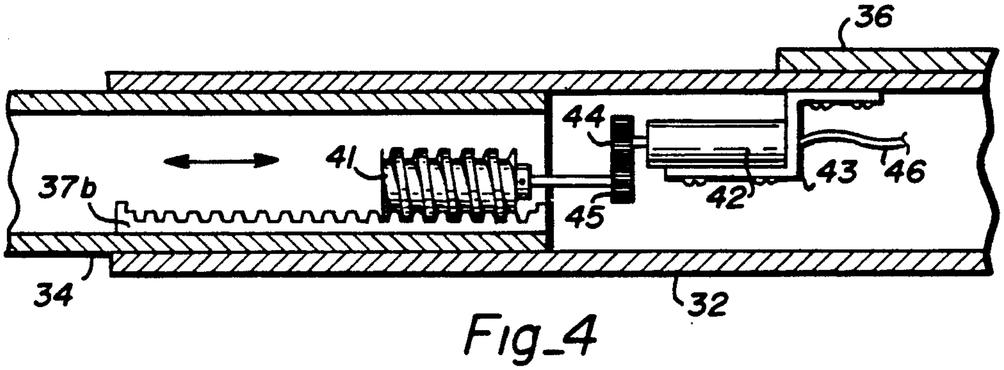
FIG. 4 is a vertical, partial section, partial schematic view showing a power drive assembly for rack and worm gear advancement/retraction mechanism for the telescoping tube of the arm assembly.

Optionally, as shown in FIG. 4, a motorized worm gear 41 can be used to engage the rack 37*b*. The motor 42 is disposed via bracket 43 in the hollow tube 32 approximately under the plate 36. Power transfer gears 44, 45 may be employed. Regular 110 volt power via cord 46 may be provided by the power cord 64, or 24 volt via the transformer/control unit 60.

PREFERRED BEST MODE

Figure 5:
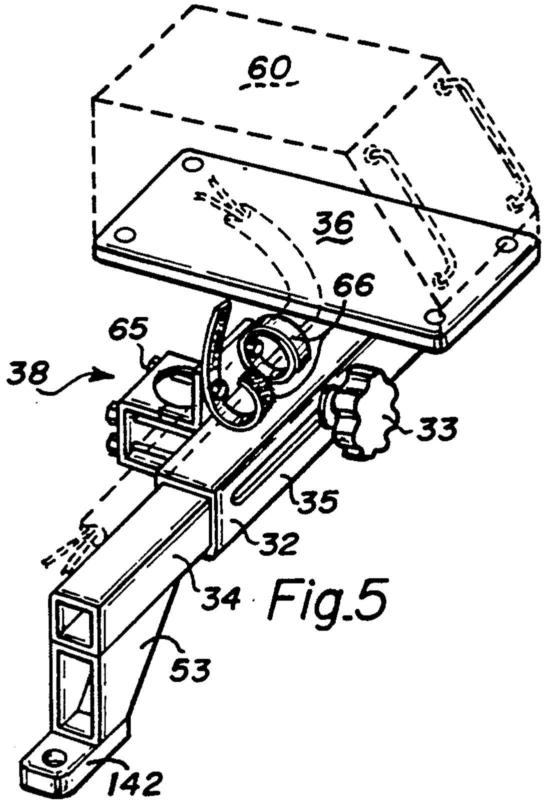
FIG. 5 is an isometric view of the preferred best mode of the invention illustrating the vertical step member securing the base of the CPM stand assembly.

As is shown in FIG. 5, the preferred best mode of the invention is constructed of mild steel. The arm assembly includes many of the same features as described above in the embodiments of FIGS. 1–4. For example, the arm assembly is secured as before to the center post of a swivel chair by means of bracket assembly 38, while the control unit 60 is supported by platform 36 and is positioned so that it is tucked under the chair and out of the way. Similarly, lateral adjustment of the arm assembly is accomplished by the telescoping feature of tube 34 within sleeve 32.

One improvement of the preferred best mode of FIG. 5 over the embodiment of FIGS. 1 and 2 is the spot welding of platform 36 onto sleeve 32 rather that attachment by threaded screws or nut and bolt fastening means. Spot welding adds strength to the bond between these two components and overcomes the problem of separation by shear forces and twisting forces that may arise when the heavy control unit 60 is installed on or removed from support platform 36.

The preferred best mode also overcomes the limitation of the height adjustment of the CPM machine. Since the height adjustment of commercially available CPM machines is limited in part by the length dimension of shaft 70 (see FIG. 2), a vertical step (extension) member 53 is provided to lower the position of the CPM machine relative to the swivel chair so that a greater range of rehabilative positions by proper vertical alignment is available to the user. Extension member 53, having a drop in the range of 3–4 inches (sufficient to still clear the floor while permitting the unobstructed use of castors 17*a–e* for rolling movement), is spot welded to the outboard end of tube 34 at one end and to tongue 142 at its other end. As before, tongue 142 is positioned to receive the threaded end 51 of lower shaft 70 of CPM machine 50 (see FIG. 2). The downward vertical displacement provided by vertical step member (extension) 53 permits proper vertical alignment of the CPM machine to permit shorter users (i.e., patients having a short torso) to exercise their upper extremity with conventionally available CPM machines in the proper position (i.e., with the upper arm substantially perpendicular to the body). This feature is also particularly useful for older users who, due to aging conditions (e.g., osteoporosis or scoliosis), may not be able to sit perfectly straight upright in the chair, thus decreasing their effective torso height and requiring the CPM machine to be lowered so that they may still benefit from a proper exercise position.

Another feature that is shown in FIG. 5 is the use of a pair of opposed hook and loop straps 66 (e.g., Velcro TM brand) that are affixed to an upstanding plate 65 associated with the bracket assembly 38. The power cords running from the back of the control unit 60 to the CPM machine 50 may be conveniently secured by tightening the straps 66 so that the cords are out of the way, yet are still capable of being quickly removed from the arm assembly for transport or control box diagnostic purposes.

OPERATION OF REHAB PATIENT POSITIONING DEVICE

A user positions him or herself on the seat 22 with his/her back supported by back rest 14. The seat height is then adjusted via gas lift lever 13 such that the user's feet firmly contact the ground. Other adjustments including seat tilt (motion of adjustment indicated by arrow C), backrest angle (angle $\alpha$), and backrest height (motion of adjustment indicated by arrow D) can be made at this time. The user then positions his or her arm within the CPM machine 50 such that the upper arm is supported by the brachial cradle 54 and the forearm is supported by the antebrachial splint 56. The telescoping arm assembly 30 is then adjusted via knob 33 in the direction shown by arrow E such that the torso cradle 58 comes to rest against the side of the user's torso. As is seen in FIG. 1 the CPM machine 50, through the vertical movement of drive member 59 (see arrow F') caused by activation of electric motor 68, provides passive abduction/adduction of the shoulder by a rotation about a pivot point of the CPM machine in the direction shown by arrow F and may optionally provide external/internal rotation about a separate axis of the CPM machine in the direction as shown by arrow G.

By itself, the CPM machines pivotally adjustable about two axes in order to assist in the proper positioning for use. For example, actuation of knob 66 permits the torso cradle 58 (including the entire brachial 54 and antebrachial 56 supports) to rotated about a pivot point away from or closer to the user's side torso area as indicated by arrow H. In addition, actuation of knob 67 permits the axial rotation about the vertical axis of shaft 70 of the entire CPM machine 50 as shown by arrow I. The positioning device 1 of the present invention also permits three more areas of adjustment for precise positioning capability, namely the lateral adjustment of the positioning arm 32 associated with knob 33 in the direction of arrow E, the axial and rotational adjustment associated with the swivel chair in the direction of arrow A, and the height adjustment of the seat 12 in the direction of arrow B. These three additional adjustment features enable a user to specifically pinpoint and/or isolate a range of motion of abduction/adduction to be performed. For example, a user who is exercising his or her right arm and shoulder may swivel the chair 12 to the left (in a counter clockwise rotation when viewed from above looking down) a desired angular amount after which the swivel chair is locked upon actuation of lock knob 26 so that an abduction/adduction of the shoulder with the shoulder effectively angled backward, respective to the user's chest, can be performed. Conversely, the user may swivel the chair inward to the right (in a clockwise direction) or toward the CPM machine 50 a desired amount after which the swivel chair is locked so that an abduction/adduction motion of the shoulder, with the arm and shoulder disposed essentially forward of the user's chest can be performed.

The positioning device of the present invention may be used in either the right or left shoulder orientation. That is, to switch from the right shoulder use position (as shown in FIG. 3) to a left shoulder use position, the arm assembly 30 is telescoped outwardly a sufficient distance for clearance to permit the chair to rotate 180°. Then, all preliminary setup adjustments for the chair and arm are performed as before. The CPM machine is then switched over to a left hand setup whereby the antebrachial splint 56 is repositioned at the opposite end of bar 57 and cable 59 is redirected from pulley 57*a* to pulley 57*b* after which it is cinched off at jam cleat 65*b*.

While the above description for the rehab patient positioning device of the present invention is directed towards positioning a shoulder CPM machine, it is understood that elbow and wrist CPM machines may be similarly combined with the arm assembly 30 and chair assembly 10 of the present invention.

It should be understood that various modifications within the scope of this invention can be made by one of ordinary skill in the art without departing from the spirit thereof. I therefore wish my invention to be defined by the scope of the appended claims as broadly as the prior art will permit, and in view of the specification if need be.

We claim:

1. Method of positioning a patient or user with respect to an upper extremity continuous passive motion machine to efficiently achieve the benefits of the rehabilitative exercise associated with the use thereof, which comprises in operative sequence the steps of:

a) providing a chair having a base assembly, a seat support, a height adjustable seat, and an adjustable lumbar support for seating and supporting the patient or user in a correct posture position with minimal spinal rotation;
b) providing an arm assembly connected to said chair having means for retainingly engaging said continuous passive motion machine at a proper exercise position including a vertical height from the floor and a lateral distance from said chair to enable a patient or user to utilize said continuous passive motion machine for selected exercise of elbow flexion and extension, shoulder forward flexion and extension, internal and external shoulder rotation, or wrist supination and pronation; and
c) providing said arm assembly with means for adjustably securing the lateral distance of said continuous passive motion machine to said chair to permit biomechanically correct continuous passive motion machine exercise by individual different patient or users having differing arm lengths and torso sizes.

2. Method of positioning a patient or user on a continuous passive motion machine as in claim 1 which includes the step of:

a) providing said chair with means for lockable rotation about its axial center to permit use of said continuous passive motion machine by either the right or left arm of a patient or user and to permit a wide range of fore and aft exercise positions of the upper arm and shoulder area with respect to the patient or user's torso.

3. Method of positioning a patient or user on a continuous passive motion machine as in claim 1 which includes the step of:

a) providing said chair with a plurality of lockable casters disposed adjacent a bottom portion of said base member to provide rolling movement of said chair.

4. Method of positioning a patient or user on a continuous passive motion machine as in claim 2 which includes the step of:

a) providing said chair with a plurality of lockable casters disposed adjacent a bottom portion of said base member to provide rolling movement of said chair.

5. Method of positioning a patient or user on a continuous passive motion machine as in claim 1 wherein said step of providing a height adjustable seat includes providing a gas lift adjustment cylinder disposed internal of said seat support.

6. Method of positioning a patient or user on a continuous passive motion machine as in claim 1 wherein said step of providing an arm assembly includes connecting said arm to said chair base assembly.

7. Method of positioning a patient or user on a continuous passive motion machine as in claim 5 wherein said step of providing an arm assembly includes connecting said arm to said chair base assembly.

8. Method of positioning a patient or user on a continuous passive motion machine as in claim 1 which includes the step of:

a) providing said base member with a plurality of radially extending, equal spaced legs arranged in a spider configuration; and
b) providing said arm adjusting means connected to said seat support adjacent the juncture between said seat support and said spider leg base member.

9. Method of positioning a patient or user on a continuous passive motion machine as in claim 8 wherein said step of providing said arm assembly includes providing a lock to secure a selected lateral distance adjustment of said arm assembly.

10. Method of positioning a patient or user on a continuous passive motion machine as in claim 1 which includes the step of:

a) providing a continuous passive motion machine for exercising the upper extremity of said patient or user.

11. Method of positioning a patient or user on a continuous passive motion machine as in claim 10 which includes the steps of:

a) adjusting an upper extremity cradle support of said continuous passive motion machine for proper vertical height to fit a patient or user; and
b) adjusting the lateral extension of said arm assembly to fit an individual patient or user.

12. Method of positioning a patient or user on a continuous passive motion machine as in claim 11 which includes the step of:

a) adjusting the height of said chair seat to fit an individual patient or user.

13. Method of positioning a patient or user on a continuous passive motion machine as in claim 11 which includes the step of:

a) providing a continuous passive motion control box mounted on said arm assembly.

* * * * *